United States Patent [19]

Hohmann et al.

[11] 4,155,921

[45] May 22, 1979

[54] PROCESS FOR THE ISOLATION OF 1,6- AND 1,7-DINITROANTHRAQUINONE

[75] Inventors: Walter Hohmann; Klaus Wunderlich, both of Leverkusen, Fed. Rep. of Germany

[73] Assignee: Bayer Aktiengesellschaft, Leverkusen, Fed. Rep. of Germany

[21] Appl. No.: 850,509

[22] Filed: Nov. 10, 1977

[30] Foreign Application Priority Data

Dec. 2, 1976 [DE] Fed. Rep. of Germany ....... 2654648

[51] Int. Cl.² .............................................. C07C 49/68
[52] U.S. Cl. .................................... 260/369; 260/707
[58] Field of Search ................................ 260/369, 707

[56] References Cited

U.S. PATENT DOCUMENTS

| 3,506,725 | 4/1970 | Sturm et al. | 260/707 |
| 3,929,841 | 12/1975 | Ackermann et al. | 260/369 |
| 3,996,252 | 12/1976 | Schroeder et al. | 260/369 |
| 4,042,604 | 8/1977 | Eilingsfeld et al. | 260/369 |
| 4,045,455 | 8/1977 | Vogel | 260/369 |
| 4,053,488 | 10/1977 | Bruenemann et al. | 260/369 |
| 4,076,734 | 2/1978 | Yamada et al. | 260/369 |

*Primary Examiner*—Allen B. Curtis
*Assistant Examiner*—Raymond Covington
*Attorney, Agent, or Firm*—Sprung, Felfe, Horn, Lynch & Kramer

[57] ABSTRACT

A process has been invented for the isolation of 1,6- and 1,7-dinitroanthraquinone by treating mixtures containing these isomers with nitrobenzene.

13 Claims, No Drawings

PROCESS FOR THE ISOLATION OF 1,6- AND 1,7-DINITROANTHRAQUINONE

The present invention relates to a process for the isolation of 1,6- and 1,7-dinitroanthraquinone by treating 1,6-/1,7-dinitroanthraquinone mixtures, which can also contain other nitro derivatives of anthraquinone, with nitrobenzene.

In the dinitration of anthraquinone, in addition to the main products, that is to say 1,5- and 1,8-dinitroanthraquinone, considerable amounts of 1,6- and 1,7-dinitroanthraquinone are also formed (compare Helv. Chim. Acta 14, 1,404 (1931)). During the separation of 1,5- and 1,8-dinitroanthraquinones from the dinitration mixtures, the 1,6- and 1,7-dinitroanthraquinones become more concentrated in the mother liquors, from which they can be isolated as a mixture, containing other nitro compounds of anthraquinone as impurities, such as is described, for example, in DT-OS (German published specification) No. 2,300,544 or in DT-AS (German published specification) No. 2,351,590.

Although in accordance with the process described in Helv. Chim. Acta. 1,6-dinitroanthraquinone could be isolated in the pure form by fractionating from sulphuric acid and then recrystallising several times from glacial acetic acid, and in accordance with the process of German Pat. No. 167,699 1,6- and 1,7-dinitroanthraquinone could be obtained by recrystallising several times, no data with respect to the crystallisation conditions and yields having been given, however, no process has yet hitherto been disclosed by which 1,6- and 1,7-dinitroanthraquinone can be obtained in good purity from 1,6/1,7-dinitroanthraquinone mixtures in a simple and economical manner.

A process has now been found for the isolations of 1,6- and 1,7-dinitroanthraquinone, which is characterised in that 1,6-/1,7-dinitroanthraquinone mixtures, which can contain other nitro derivatives of anthraquinone, are extracted with about 2.5 to 8.5 times the amount of weight of nitrobenzene, relative to the 1,6-/1,7-dinitroanthraquinone mixture employed, at about 85° to 135° C., the extraction residue is washed with nitrobenzene, 1,7-dinitroanthraquinone remaining behind, and 1,6-dinitroanthraquinone is precipitated from the extract, optionally mixed with the wash filtrate, by cooling to about 40° to 75° C. and filtered off, and the residue is washed with nitrobenzene.

In this procedure, 1,7-dinitroanthraquinone is obtained as the residue of an extraction and 1,6-dinitroanthraquinone separates out of the extract by cooling. In detail, the process is carried out by treating a mixture of 1,6- and 1,7-dinitroanthraquinone, which optionally contains other nitro compounds of anthraquinone as impurities, with about 2.5 to 8.5 times, preferably with about 5 to 7 times, the amount of weight of nitrobenzene at a temperature from about 80° to 135° C., preferably at a temperature from about 90° to 110° C., isolating the 1,7-dinitroanthraquinone, which has not dissolved, at the same temperature, freeing this from the adhering mother liquor by treatment with nitrobenzene and drying it, subsequently separating 1,6-dinitroanthraquinone out of the extract, alone or mixed with the washing filtrate, by cooling to about 40° to 75° C., isolating this, freeing it from adhering mother liquor by treatment with nitrobenzene and drying it.

The form in which the crude 1,6-/1,7-dinitroanthraquinone mixture is employed is of importance for the isolation of 1,7-dinitroanthraquinone by extraction. So that the other dinitroanthraquinones are dissolved out to the largest possible extent in as short a time as possible, the 1,6-/1,7-dinitroanthraquinone mixture should be employed in a finely divided form, for example in the ground form. Furthermore, it is advantageous to ensure thorough mixing of the solid and solution by suitable measures, for example stirring.

The extraction times are not critical. In the case of a sufficient fine division and thorough mixing, almost optimum separation effects are already achieved after about 30 minutes. Longer extraction times do not give substantially better separation effects, but are also not disadvantageous. A preferred extraction time is about 1 to 3 hours.

Washing the 1,7-dinitroanthraquinone, which has been filtered off, with nitrobenzene preferably serves to displace the mother liquor from the extraction residue. A purification effect of the solid content is thereby achieved at most to a small extent. The temperature of the solvent used for the washing also plays no significant role in the purification of the 1,7-dinitroanthraquinone. The extraction residue is preferably washed with solvent at room temperature. The amount used for washing is relatively small and is about 10 to 25% of the amount of nitrobenzene employed for the extraction.

It is surprising that the separation and purification of the 1,7-dinitroanthraquinone from the crude 1,6-/1,7-dinitroanthraquinone mixture succeeds by extraction only. By recrystallisating the 1,6-/1,7-dinitroanthraquinone mixtures in nitrobenzene, neither the yields nor the degrees of purity, such as are obtained in the extraction, are achieved. Comparison Example 6, hereinafter, demonstrates this.

The separation of 1,6-dinitroanthraquinone from the extract or from the extract/wash filtrate mixture is accomplished by cooling the extract or the extract/wash filtrate mixture to about 40° to 75° C., preferably to about 50° to 65° C. If it should be necessary, the extract or the extract/wash filtrate mixture can be previously warmed until a clear solution forms.

It is surprising that during this procedure only 1,6-dinitroanthraquinone precipitates although the extract is saturated with 1,7-dinitroanthraquinone and the solubility curve of 1,7-dinitroanthraquinone exhibits normal behaviour, that is to say a decrease in the solubility with decreasing temperature. 1,6-Dinitroanthraquinone can therefore be separated out of a solution which is supersaturated with 1,7-dinitroanthraquinone, it being immaterial whether or not the solution is stirred during the crystallisation. The same yields and degrees of purity of 1,6-dinitroanthraquinone are obtained with or without stirring. However, on stirring 1,6-dinitroanthraquinone already precipitates at temperatures which are a little higher. In this procedure it is advantageous when the mixture is subsequently further stirred for some time after the precipitation. Further stirring times of up to 3 hours are possible (compare Example 2).

The amounts of solvent required for the extraction and the extraction temperatures are related to one another in a particular manner. Good results, in the sense of the process according to the invention, are achieved in the extraction of 1,6-/1,7-dinitroanthraquinone mixtures when, in the abovementioned temperature and solvent range, preferably large amounts of solvent are combined with low temperatures, small amounts of solvent are combined with high temperatures and medium amounts of solvent are combined with medium temperatures.

It has, therefore, proved advantageous when the extraction is carried out in a temperature range from about 85° to 135° C. with about 2.5 to 8.5 times the amount by weight of nitrobenzene, relative to the crude 1,6-/1,7-dinitroanthraquinone mixture employed. When the extraction is carried out in the temperature range from about 90° to 110° C., about 5 to 7 times the amount by weight of nitrobenzene is preferably employed.

The nature and amount of the impurities and the ratio of 1,6- to 1,7-dinitroanthraquinone in the crude 1,6-/1,7-dinitroanthraquinone mixture is important for the isolation of 1,6- and 1,7-dinitroanthraquinone by the process according to the invention.

Although in principle 1,6-/1,7-dinitroanthraquinone mixtures of any desired origin can be used for the process according to the invention, those mixtures which are obtained by fractionating from anthraquinone dinitration mixtures are preferably employed.

As the examples show, separations by the process according to the invention are still possible when not more than about 7% by weight, of 1,5-dinitroanthraquinone and less than about 25% by weight of 1,8-dinitroanthraquinone are present in the 1,6-/1,7-dinitroanthraquinone mixture. Preferred mixtures contain less than about 18%, by weight, of 1,8-dinitroanthraquinone and less than 3%, by weight, of 1,5-dinitroanthraquinone.

It is understandable that the yields and/or quality of 1,6- and 1,7-dinitroanthraquinone improve, the lower the contents of 1,5- and/or 1,8-dinitroanthraquinone in the dinitroanthraquinone mixture, since 1,5-dinitroanthraquinone and 1,8-dinitroanthraquinone are distinctly less soluble in nitrobenzene than 1,7-dinitroanthraquinone or 1,6-dinitroanthraquinone. In general, increased 1,5- or 1,8-dinitroanthraquinone proportions in the 1,6/1,7-dinitroanthraquinone mixture necessitate temperatures during the separation which are a little higher, that is to say temperatures in the upper half of the temperature ranges indicated.

Not only the absolute content of impurities, but also their ratio to the content of 1,6-/1,7-dinitroanthraquinone is important. The smaller the ratio of the sum of 1,6- and 1,7-dinitroanthraquinone to the sum of the impurities, the lower the yields and/or qualities obtained.

With regard to the ratio of 1,6-dinitroanthraquinone to 1,7-dinitroanthraquinone, the situation is that in general separations are still possible in the range of a ratio from about 0,1:1 to 2.5:1 by the process according to the invention. The separation yields which can be achieved are shifted, within this range, more in favour of the α,β-isomer, present in excess, the more the ratio is shifted towards the limits.

The total content of 1,6- and 1,7-dinitroanthraquinone in the separation mixtures should preferably not be below about 60% by weight, more preferably at least in the range about 65 to 70% by weight.

Since during the dinitration of anthraquinone 1,6- and 1,7-dinitroanthraquinone form in almost equal amounts, independently of the nitration process chosen, after the successive or simultaneous separation of the majority of 1,5- and 1,8-dinitroanthraquinone from the nitration mixtures by suitable measures, for example cooling, dilution with water, concentration of the filtrates, alone or in combination, and subsequent isolation of the products which have precipitated, fractions are obtained which in general, from the point of view of their composition, fulfil the requirements to be placed on the material employed for the process according to the invention. For example 1,6-/1,7-dinitroanthraquinone mixtures which are obtainable in accordance with the processes described in DT-AS (German published specification) No. 2,351,590, DT-AS (German published specification) No. 1,042,160 and DT-OS (German published specification) No. 2,300,544 can be employed.

Even in the case of dinitroanthraquinone mixtures, with 1,6-/1,7-dinitroanthraquinone as the main consituent, in which the ratio of 1,6-dinitroanthraquinone to 1,7-dinitroanthraquinone or the contents of 1,5- and/or 1,8-dinitroanthraquinone are outside the given limits or which contain a particularly high proportion of impurities, at least one of the α,β-isomeric dinitroanthraquinone can still be obtained in good purity by the process according to the invention, as is demonstrated in Example 5.

The sepration yields for 1,7-dinitroanthraquinone are in the range from about 60 to 85% and those for 1,6-dinitroanthraquinone are in the range from about 35 to 65%. The degree of purity of both isomers is over 90%; for 1,6-dinitroanthraquinone it is in the range from 95 to 99,5% and for 1,7-dinitroanthraquinone it is in the range from 94 to 97%.

1,6- and 1,7-dinitroanthraquinone are valuable intermediate products for dyestuffs. Thus, for example, according to German Offenlegungsschriften (German published specifications) Nos. 2,300,544, 2,304,200 and 2,300,592, violet disperse dyestuffs with a good to very good affinity and fastness properties are obtained by selectively replacing the nitro group in the α-position by arylamines.

In the examples which follow, the analyses are based on quantittative thin layer of high-pressure liquid chromatography; parts denote parts by weight, unless expressly indicated otherwise, and the temperatures are given in ° C. In the Examples the abbreviation "NA" denotes nitroanthraquinone and "DNA" denotes dinitroanthraquinone.

EXAMPLE 1

(A) 500 g of a dinitroanthraquinone mixture of the following composition: 40.3% of 1,6-DNA, 38,5% of 1,7-DNA, 16,9% of 1,8-DNA, 2,4% of 1,5-DNA, 0.2% of 1-NA, 0.2% of 2,6-DNA and 0.2% of 2,7-DNA are stirred, in the ground form, in 2,500 ml of nitrobenzene for 2 hours at 90°–92°, the suspension is filtered at the same temperature and the residue is washed with 250 ml of cold nitrobenzene and then freed from solvent at 140° in vacuo. This gives 145.5 g of 1,7-dinitroanthraquinone having the following analysis:
1,7-DNA: 96.0%
1,6-DNA: 2.3%
1,5-DNA: 0.4%
1,8-DNA: 1,0%

The separation yield for 1,7-DNA is 73%.

The mother liquor and the nitrobenzene washing are warmed until a clear solution is obtained and allowed to cool to 55°–60°, without stirring, the crystals which separate out are filtered off on a pre-warmed suction filter and washed with 250 ml of cold nitrobenzene and the material on the filter is dried in vacuo at 140°. This gives 96.3 g of 1,6-dinitroanthraquinone having the following analysis:
1,6-DNA: 97,4%
1,7-DNA: 1,1%

1,5-DNA: 0,6%
1,8-DNA: 0,8%

The separation yield for 1,6-DNA is 46%.

(B) The product employed in (A) can be obtained as follows:

400 g of anthraquinone are introduced into 830 ml of oleum (20% strength) in the course of 2 hours and 1,00 g of mixed acid, consisting of 33% of nitric acid (100% strength) and 67% of $H_2SO_4$ (100% strength) are then added uniformly in the course of 3 hours. During this procedure, the temperature is allowed to rise to 50° C. The mixture is then warmed to 95° C. in the course of 2 hours and is kept at this temperature for a further 2 hours. It is cooled to 20° to 25° C. and stirred for a further 2 hours, and the precipitate is filtered off and washed with 1,000 ml of cold $H_2SO_4$ (96% strength). The material on the filter, washed until neutral and dried, gives 364 g of a mixture which consists of the extent of 49% of 1,5-DNA and to the extent of 41% of 1,8-DNA.

The mother liquor and washing (~2,100 g) are warmed until a clear solution is obtained, then cooled to 70° C., 180 ml of water are added after about 1 hour, the mixture is subsequently stirred for 30 minutes at 80° C. and the precipitate is filtered off, washed with 250 ml of 88–90% strength $H_2SO_4$ at 80°, washed with hot water until neutral and dried.

132 g of the composition indicated in (A) are obtained.

EXAMPLE 2

100 g of a dinitroanthraquinone mixture of the composition indicated in Example 1 (A) are stirred in 500 ml of nitrobenzene for 2 hours at 95°, the suspension is filtered at the same temperature and the residue is washed with 50 ml of cold nitrobenzene and then freed from solvent at 140° in vacuo. This gives 26.1 g of 1,7-dinitro-anthraquinone of the following composition.
1,7-DNA: 96,2%
1,6-DNA: 2,5%
1,5-DNA: 0,2%
1,8-DNA: 0,8%

The separation yield for 1,7-DNA is 65%.

The mother liquor filtrate is warmed until a clear solution is obtained, cooled to 70° C., whilst stirring, and stirred for a further 3 hours at the same temperature. Filtration at 70° C. and washing the residue with 50 ml of cold nitrobenzene gives 16.6 g of 1,6-dinitroanthraquinone of the following composition:
1,6-DNA: 97,1%
1,7-DNA: 0,5%
1,5-DNA: 1,2%
1,8-DNA: 0,2%

The separation yield for 1,6-DNA is 40%.

EXAMPLE 3

100 g of dinitroanthraquinone mixture of the composition described in Example 1 (A) are employed and stirred with B ml of nitrobenzene at C° C. for A hours and the precipitate is filtered off at C° C., washed with 50 ml of nitrobenzene and dried. D g of 1,7-dinitroanthraquinone of the composition E are obtained.

The mixture of extract+washing gives H g of 1,6 dinitroanthraquinone of the composition I when the mixture is either cooled to F° C., without stirring, and filtered and the residue is washed with 50 ml of nitrobenzene and dried, or the mixture is cooled to F° C., whilst stirring, stirred for a further 6 hours at F° C. and filtered and the residue is washed with 50 ml of nitrobenzene and dried.

| Serial No. | A hrs. | B ml | C °C. | D g | E (%) of DNA 1,6- | 1,7- | 1,5- | 1,8- | stirred = + not stirred = − | F °C. | G hrs. | H g | I (%) of DNA 1,6- | 1,7- | 1,5- | 1,8- |
|---|---|---|---|---|---|---|---|---|---|---|---|---|---|---|---|---|
| 1 | 2 | 200 | 135 | 22.2 | 2.9 | 94.3 | 0.6 | 1.5 | + | 105 | 1 | 12.3 | 97.1 | 1.0 | 0.9 | 0.5 |
| 2 | 2 | 300 | 120 | 22.7 | 2.8 | 95.4 | 0.4 | 1.0 | − | 70 | — | 18.9 | 96.3 | 1.7 | 0.7 | 0.8 |
| 3 | 2 | 300 | 120 | 21.4 | 3.2 | 95.0 | 0.3 | 1.2 | + | 70 | 0 | 19.3 | 97.1 | 1.0 | 0.5 | 0.1 |
| 4 | 2 | 500 | 85 | 31.2 | 6.6 | 91.5 | 0.6 | 1.0 | − | 58 | — | 14.6 | 97.1 | 0.9 | 0.6 | 0.2 |
| 5 | 0.5 | 500 | 95 | 26.0 | 2.7 | 95.7 | 0.4 | 0.9 | − | 56 | — | 18.0 | 97.2 | 1.0 | 0.7 | 0.3 |
| 6 | 6 | 500 | 95 | 26.6 | 2.6 | 95.6 | 0.5 | 0.9 | − | 56 | — | 18.2 | 96.0 | 1.1 | 0.8 | 0.4 |
| 7 | 2 | 500 | 100 | 24.2 | 1.9 | 96.6 | 0.3 | 0.8 | − | 65 | — | 11.5 | 97.0 | 0.8 | 0.6 | 0.2 |
| 8 | 2 | 500 | 110 | 20.2 | 2.1 | 96.7 | 0.2 | 0.8 | − | 37 | — | 22.4 | 90.4 | 7.0 | 1.0 | 0.7 |
| 9 | 2 | 500 | 95 | 25.1 | 3.5 | 95.0 | 0.4 | 1.0 | + | 70 | 1 | 15.3 | 97.1 | 0.7 | 0.4 | — |
| 10 | 5 | 500 | 100 | 24.2 | 2.2 | 95.1 | 0.2 | 1.3 | − | 55 | 1 | 20.6 | 97.2 | 1.0 | 0.7 | 0.3 |
| 11 | 2 | 700 | 85 | 25.8 | 3.0 | 95.2 | 0.2 | 1.2 | − | 45 | — | 12.6 | 96.9 | 0.7 | 0.9 | 0.6 |
| 12 | 2 | 700 | 90 | 1.0 | 2.1 | 96.2 | 0.3 | 1.0 | + | 40 | 0 | 20.5 | 95.9 | 1.6 | 0.6 | 0.4 |

EXAMPLE 4

40 g of a mixture of 1,6/1,7-dinitroanthraquinone of the composition 73,1% of 1,7-DNA, 24,2% of 1,6-DNA, 0,7% of 1,5-DNA, 1.2% of 1,8-DNA, 0.3% of 1-NA and 0.2% of 2-NA are extracted with 200 ml of nitrobenzene for 2 hours at 90° C. and filtered at the same temperature and the residue is washed with 40 ml of nitrobenzene. Drying gives 25.5 g of 1,7-dinitroanthraquinone of the following composition:
1,7-DNA: 95,6%
1,5-DNA: 0,4%
1,6-DNA: 2,1%
1,8-DNA: 1,5%

Separation yield of 1,7-DNA: 83%.

The filtrate and washing are warmed until a solution is obtained, cooled to 50° C., whilst stirring, and stirred for a further hour at 50° C. Filtration, washing with 40 ml of nitrobenzene and drying gives 12.1 g of 1,6-dinitroanthraquinone of the following composition:
1,6-DNA: 98.1%
1,5-DNA: 0.2%
1,7-DNA: 0.7%
1,8-DNA: 0.2%

Separation yield of 1,6-DNA: 49%.

EXAMPLE 5

100 g of a dinitroanthraquinone mixture of the composition A are employed and are stirred with C ml of nitrobenzene at D° C. for B hours, the precipitate is filtered off at D° C. and washed with 50 ml of nitrobenzene and the material on the filter is freed from nitrobenzene in vacuo. E g of 1,7-dinitro-anthraquinone of the composition F are obtained.

The mixture of extract+washing gives I g of 1,6-dinitroanthraquinone of the composition K when the clear solution is either cooled to G° C., without stirring, and filtered and the residue is washed with 50 ml of nitrobenzene and freed from nitrobenzene by drying under reduced pressure, or the mixture is cooled to G° C., whilst stirring, stirred for a further H hours at G° C. and filtered and the residue is washed with 50 ml of nitrobenzene and freed from nitrobenzene by drying under reduced pressure.

| Serial No. | A % of DNA 1,5- | 1,6- | 1,7- | 1,8- | 2,6/2,7- | Hydroxy DNA's e | B hrs. | C ml | D °C. | E g | 1,5- | 1,6- | 1,7- | 1,8- | °C. | stirred = + not stirred = − | H hrs. | I g | 1,5- | K % of DNA 1,6- | 1,7- | 1,8- |
|---|---|---|---|---|---|---|---|---|---|---|---|---|---|---|---|---|---|---|---|---|---|---|
| 1[1] | 1.6 | 41.8 | 38.6 | 12.0 | 0.9 | 1.2 | 2 | 500 | 92 | 31.2 | 0.3 | 3.1 | 95.1 | 0.8 | 60 | − | — | 16.8 | 0.3 | 97.8 | 0.8 | 1.0 |
| 2 | 2.2 | 3.3 | 35.7 | 22.2 | 0.4 | 0.7 | 2 | 465 | 110 | 22.7 | 0.5 | 2.6 | 92.6 | 3.5 | 60 | + | 0 | 15.6 | 0.8 | 96.6 | 0.7 | 1.3 |
| 3 | " | " | " | " | " | " | 2 | 465 | 110 | 18.2 | 0.4 | 2.8 | 95.3 | 1.2 | 60 | + | 0 | 12.9 | 0.6 | 97.1 | 0.8 | 0.4 |
| 4 | 6.4 | 38.6 | 36.8 | 16.2 | 0.5 | 0.8 | 2 | 500 | 105 | 21.6 | 1.1 | 2.7 | 95.1 | 0.8 | 52 | + | — | 14.9 | 1.0 | 96.3 | 0.7 | 0.8 |
| 5 | " | " | " | " | " | " | 2 | 500 | 105 | 24.5 | 8.5 | 2.5 | 87.0 | 1.5 | 65 | − | 1 | 18.6 | 0.8 | 96.3 | 0.8 | 0.8 |
| 6[2] | 6.3 | 39.7 | 25.7 | 14.9 | 2.2 | 1.1 | 2 | 500 | 100 | 14.4 | 15.2 | 2.6 | 80.4 | 1.8 | 45 | + | — | 16.0 | 1.2 | 96.2 | 1.0 | 0.8 |
| 7 | 4.6 | 39.7 | 37.6 | 16.4 | 0.4 | 0.8 | 2 | 500 | 105 | 21.6 | 0.6 | 3.2 | 95.0 | 1.1 | 51 | + | 1 | 15.3 | 1.2 | 96.0 | 1.2 | 0.6 |
| 8[3] | 4.7 | 32.1 | 28.3 | 17.2 | 4 | 7.7 | 2 | 500 | 85 | 22.3 | 2.4 | 2.5 | 85.2 | 9.8 | 50 | − | 1 | 7.4 | 0.7 | 96.4 | 1.1 | 0.2 |
| 9 | " | " | " | " | " | " | 2 | 500 | 90 | 16.6 | 0.8 | 2.8 | 95.0 | 1.2 | 55 | + | 1 | 5.9 | 1.2 | 96.7 | 1.0 | 0.7 |
| 10[4] | 0.7 | 33.5 | 63.7 | 1.1 | 0.1 | 0.4 | 2 | 500 | 90° | 54.8 | 0.4 | 2.1 | 96.2 | 0.7 | 50 | + | 1 | 19.3 | 0.2 | 98.3 | 0.9 | 0.2 |
| 11[4] | 0.9 | 48.1 | 47.6 | 2.2 | — | 0.3 | 2 | 500 | 100° | 30.4 | 0.6 | 2.3 | 95.8 | 0.2 | 75 | + | — | 12.2 | 0.2 | 96.1 | 2.4 | 0.9 |
| 12[4] | 0.2 | 38.1 | 38.4 | 2.4 | " | 0.3 | 2 | 500 | 115° | 18.4 | 0.1 | 3.5 | 95.3 | 0.8 | 67 | + | — | 28.6 | — | 97.5 | 1.1 | 0.4 |
| 13[4] | 1.1 | 32.0 | 24.6 | 1.8 | 0.1 | 0.2 | 2 | 550 | 115° | 10.9 | 0.3 | 4.1 | 94.8 | 0.4 | 71 | − | — | 31.7 | 0.7 | 96.0 | 1.3 | 1.0 |
| 14 | 8.2 | 38.7 | 25.7 | 14.9 | 2.2 | 0.9 | 2 | 500 | 105° | 10.6 | 18.6 | 2.8 | 75.1 | 1.8 | 45 | − | — | 18.3 | 1.1 | 97.2 | 1.1 | 0.4 |
| 15 | 4.7 | 30.1 | 27.3 | 16.2 | 4.8 | 6.7 | 2 | 400 | 98° | 14.0 | 1.1 | 2.9 | 95.1 | 0.6 | 40 | + | — | 18.6 | 0.7 | 94.7 | 1.4 | 12.4 |

Product of the composition A
[1]obtained according to DT-OS (German Published Specification) 2,300,591, Example 1c
[2]obtained according to DT-OS (German Published Specification) 2,351,590, Example 2, fraction IIIb
[3]obtained according to DT-OS (German Published Specification) 2,351,590, Example 2, obtained by making a paste of the mother liquor from fraction IIIa, washing until neutral and drying.
[4]obtained by mixing pure 1,6- and 1,7-dinitroanthraquinone

EXAMPLE 6

(Comparison Example)

100 g of a dinitroanthraquinone mixture of the composition given in Example 1 (A) are dissolved, in the ground form, in 500 ml of nitrobenzene at 140°, the solution is cooled to 100° C., whilst stirring, and stirred for A hours at 100° and the precipitate is filtered off at the same temperature, washed with 50 ml of nitrobenzene and freed from nitrobenzene in vacuo. This gives B g of 1,7-dinitro-anthraquinone of the composition C.

| Serial No. | A hrs. | B g | C % of DNA | | | |
|---|---|---|---|---|---|---|
| 1 | 2 | 16.2 | 90.4 | 0.5 | 8.4 | 0.5 |
| 2 | 2 | 15.6 | 89.1 | 0.7 | 8.7 | 0.9 |
| 3 | 2 | 16.0 | 84.9 | 0.9 | 12.1 | 1.1 |
| 4 | 2 | 18.0 | 90.0 | 0.2 | 7.9 | 1.4 |

Compared with Example 3, Table Example No. 7, a clearly poorer quality of 1,7-dinitro-anthraquinone is obtained in a substantially lower yield. Extraction is thus superior to recrystallisation.

What is claimed is:

1. Process for the isolation of 1,6- and 1,7-dinitroanthraquinone which comprises extracting a 1,6/1,7-dinitroanthraquinone mixtures, optionally containing other nitro derivatives of anthraquinone, with about 2.5 to 8.5 times the amount by weight of nitrobenzene, relative to the 1,6/1,7-dinitroanthraquinone mixture employed, at about 85° to 135° C., washing the extraction residue with nitrobenzene, separating the 1,7-dinitroanthraquinone which remains behind, and precipitating the 1,6-dinitroanthraquinone from the extract, by cooling to about 40° to 75° C., filtering and washing the residue with nitrobenzene.

2. Process according to claim 1, wherein the 1,6-dinitroanthraquinone containing 1,7-dinitroanthraquinone is mixed with the wash-filtrate before cooling to about 40° to 75° C.

3. Process according to claim 1, wherein the extraction of the 1,6/1,7-dinitroanthraquinone mixture is carried out at 90° to 110° C.

4. Process according to claim 1, wherein the extraction of 1,6/1,7-dinitroanthraquinone mixture is carried out with 5 to 7 times the amount by weight, relative to the 1,6/1,7-dinitroanthraquinone mixture employed.

5. Process according to claim 2, wherein 1,6-dinitroanthraquinone is separated off by cooling the mixture of extract and wash filtrate to about 50° to 65° C.

6. Process according to claim 1, wherein the 1,6/1,7-dinitroanthraquinone mixture is extracted for about 1 to 3 hours.

7. Process according to claim 1, wherein 1,6/1,7-dinitroanthraquinone mixture which contains at least 60% of 1,6- and 1,7-dinitroanthraquinone is employed as the starting material.

8. Process according to claim 1, wherein a 1,6/1,7-dinitroanthraquinone mixture in which the ratio of 1,6-dinitroanthraquinone to 1,7-dinitroanthraquinone is about 0.1:1 to 2,5:1 is employed as the starting material.

9. Process according to claim 1, wherein a 1,6/1,7-dinitroanthraquinone mixture which contains less than about 25% of 1,8-dinitroanthraquinone is employed as the starting material.

10. Process according to claim 1, wherein a 1,6/1,7-dinitroanthraquinone mixture which contains less than about 7% of 1,5-dinitroanthraquinone is employed as the starting material.

11. Process according to claim 1, wherein a 1,6/1,7-dinitroanthraquinone mixture which contains less than about 18% of 1,8-dinitroanthraquinone and less than 3% of 1,5-dinitroanthraquinone is employed as the starting material.

12. Process according to claim 1, wherein the mixture is stirred during the 1,6-dinitroanthraquinone separation.

13. Process according to claim 1, wherein a 1,6/1,7-dinitroanthraquinone mixture which has been obtained from nitration mixtures of anthraquinone by fractionating once is employed as the starting material.

* * * * *